United States Patent
Peng et al.

(10) Patent No.: US 7,977,426 B2
(45) Date of Patent: Jul. 12, 2011

(54) FLUOROALKYL ETHER SULFONATE SURFACTANTS

(75) Inventors: Sheng Peng, Hockessin, DE (US); Ming-Hong Hung, Wilmington, DE (US); Christopher P. Junk, Wilmington, DE (US); Phan Linh Tang, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 317 days.

(21) Appl. No.: 12/270,120

(22) Filed: Nov. 13, 2008

(65) Prior Publication Data
US 2010/0120980 A1  May 13, 2010

(51) Int. Cl.
C08K 3/06 (2006.01)
(52) U.S. Cl. ........................................ 524/742
(58) Field of Classification Search .................... 524/742
See application file for complete search history.

(56) References Cited

U.S. PATENT DOCUMENTS

| | | | |
|---|---|---|---|
| 3,282,875 A | | 11/1966 | Connolly et al. |
| 3,821,290 A | * | 6/1974 | Anello et al. |
| 4,012,441 A | | 3/1977 | Pontoglio et al. |
| 4,358,545 A | | 11/1982 | Ezzell et al. |
| 4,380,618 A | | 4/1983 | Khan et al. |
| 4,472,290 A | * | 9/1984 | Caporiccio et al. |
| 4,723,016 A | * | 2/1988 | Chenard et al. |
| 4,940,525 A | | 7/1990 | Ezzell et al. |
| 5,536,754 A | | 7/1996 | Feiring |
| 5,637,748 A | | 6/1997 | Hung et al. |
| 5,763,552 A | | 6/1998 | Feiring et al. |
| 6,177,196 B1 | | 1/2001 | Brothers et al. |
| 6,300,445 B1 | | 10/2001 | Hung et al. |
| 6,534,470 B1 | | 3/2003 | Durbut et al. |
| 6,555,639 B2 | | 4/2003 | Apostolo et al. |
| 6,613,730 B1 | | 9/2003 | Durbut et al. |
| 6,767,977 B2 | | 7/2004 | Arcella et al. |
| 6,774,164 B2 | | 8/2004 | Lyons et al. |
| 6,855,476 B2 | * | 2/2005 | Ferreira et al. |
| 6,858,124 B2 | * | 2/2005 | Zazzera et al. |
| 7,094,839 B2 | | 8/2006 | Grootaert et al. |
| 7,306,747 B2 | | 12/2007 | Visca et al. |
| 2006/0166007 A1 | | 7/2006 | Kent et al. |
| 2007/0019708 A1 | * | 1/2007 | Shiflett et al. |
| 2007/0066853 A1 | * | 3/2007 | Harmer et al. ................ 568/679 |
| 2007/0117914 A1 | | 5/2007 | Hintzer et al. |
| 2008/0093582 A1 | | 4/2008 | Nagai et al. |

FOREIGN PATENT DOCUMENTS

| | | |
|---|---|---|
| CA | 842252 | 5/1970 |
| EP | 0466483 A1 * | 1/1992 |
| EP | 0596485 A1 * | 5/1994 |
| JP | 52023023 | 5/1977 |
| JP | 06009542 | 2/1994 |
| JP | 08044066 | 2/1996 |
| JP | 10036501 | 2/1998 |
| JP | 2003292989 | 10/2003 |

OTHER PUBLICATIONS

Chun Zhou et al., Chemical Durability Studies of Perfluorinated Sulphonic Acid Polymers and Model Compounds Under Mimic Fuel Cell Conditions, Macromolecules, Nov. 2, 2007, pp. 8695-8707, vol. 40, No. 24, American Chemical Society, Washington, DC.*
Wenbiao Cen et al., 1,1,2,2-Tetrafluoro-2-(polyfluoroalkoxy)-ethanesulphonic acids, 1,1,2,2-tetrafluoro-2-(perfluoroalkoxy) ethanesulphonic acids, and 2,2'-oxybis(1,1,2,2-tetrafluoroethanesulphonic acid), Inorganic Chemistry, Jan. 1, 1988, pp. 1376-1377, vol. 27, No. 8, American Chemical Society, Washington, DC.*
Honda et al., Molecular aggregation structure and surface properties of poly(fluoroalkyl) thin films. Macromolecules (2005), 38, 5699-5705, American Chemical Society.
Miyatake et al., Synthesis and properties of novel sulfonated arylene ether/fluorinated alkane copolymers. Macromolecules (2001), 34, 2065-2071, American Chemical Society.
Torcheux et al., Effect of a special additive on the performance of standy valve-regulated lead acid batteries, Journal of Power Sources (1999), 78(1-2), 147-155, Elsevier Science S.A.

* cited by examiner

*Primary Examiner* — Edward J Cain
(74) *Attorney, Agent, or Firm* — Nancy S. Mayer

(57) ABSTRACT

A compound of Formula (1)

$$R_f-O-(CXX')_m-(CY_2)_n SO_3 M \qquad (1)$$

wherein
$R_f$ is a $C_1$ to $C_4$ linear or branched perfluoroalkyl group,
X and X' are each independently H or F, provided that at least one of X or X' is F,
each Y is independently H or F,
m is an integer from 1 to 4,
n is an integer from 1 to 2, and
M is H, $NH_4$, Li, Na or K,
provided that when CXX' is CHF or CFH, then n is 2.

17 Claims, No Drawings

FLUOROALKYL ETHER SULFONATE SURFACTANTS

FIELD OF THE INVENTION

This invention relates to a process for the dispersion polymerization of a fluorinated olefin monomer in an aqueous polymerization medium in the presence of a fluoroalkyl ether sulfonate surfactant.

BACKGROUND OF THE INVENTION

Dispersion processes for polymerizing fluoro olefin monomers in aqueous media employ a surfactant to provide stability to the aqueous dispersion of particles of the resulting fluoropolymer. Different surfactants are chosen for use in dispersion polymerization because of their influence on reaction rate, dispersed fluoropolymer particle size, dispersion stability, color and the like.

Fluorosurfactants used in the polymerization are usually anionic, non-telogenic, soluble in water and stable to reaction conditions. The fluorosurfactants as disclosed in U.S. Pat. No. 6,774,164 contain perfluoroalkyl groups having 4 to 18 carbon atoms. It is also known that the presence of a fluorocarbon "tail" in the hydrophobic segment of surfactants provides extremely low surface energy. Such fluorinated surfactants are much more surface active than their hydrocarbon counterparts. For surfactants and surface treatment agents with fluorochemical chains, longer perfluoroalkyl chains contain a higher percentage of fluorine at a given concentration and typically provide better performance. However, the fluorinated materials derived from longer perfluoroalkyl chains are more expensive.

Honda et al, in Macromolecules, 2005, 38, 5699-5705 teach that for perfluoroalkyl chains of greater than 8 carbons, orientation of the perfluoroalkyl groups, designated $R_f$ groups, is maintained in a parallel configuration while for such chains having less than 6 carbons, reorientation occurs. This reorientation decreases surface properties such as contact angle. Therefore, it is desirable to reduce the fluorine content with delivery of the same or higher performance.

It is desirable to provide new and improved fluorinated surfactants in which the perfluoroalkyl group of the prior art is replaced by partially fluorinated terminal groups which show increased fluorine efficiency. By "fluorine efficiency" is meant the ability to use a minimum amount of fluorochemical to obtain a desired surface effect. A surfactant having high fluorine efficiency generates the same or greater level of surface effect using a lower amount of fluorine than a comparative surfactant. The present invention provides such improved fluorinated surfactants.

SUMMARY OF THE INVENTION

The present invention comprises a compound of formula (1)

$$R_f-O-(CXX')_m-(CY_2)_n SO_3 M \qquad (1)$$

wherein
$R_f$ is a $C_1$ to $C_4$ linear or branched perfluoroalkyl group,
X and X' are each independently H or F, provided that at least one of X or X' is F,
each Y is independently H or F,
m is an integer from 1 to 4,
n is an integer from 1 to 2, and
M is H, $NH_4$, Li, Na or K,
provided that when CXX' is CHF or CFH, then n is 2.

The present invention further comprises a process comprising polymerizing at least one fluorinated olefin monomer in an aqueous medium in the presence of a compound of formula (1A)

$$R_f-O-(CXX')_m-(CY_2)_n SO_3 M \qquad (1A)$$

wherein
$R_f$ is a $C_1$ to $C_4$ linear or branched perfluoroalkyl group,
X and X' are each independently H or F, provided that at least one of X or X' is F,
each Y is independently H or F,
m is an integer from 1 to 4,
n is an integer from 1 to 2, and
M is H, $NH_4$, Li, Na or K.

The present invention further comprises a method of altering the surface behavior of a liquid comprising adding to the liquid a compound of formula (1A) as defined above.

DETAILED DESCRIPTION OF THE INVENTION

Trademarks used herein are denoted by capitalization.

The term "fluoroalkyl ether sulfonate" as used herein refers to a fluorinated sulfonic acid or a fluoroalkyl ether sulfonate salt, or a mixture thereof.

The present invention provides a fluoroalkyl ether sulfonate surfactant which contains shorter fluoroalkyl chains having no more than 4 continuous carbons. Furthermore, said fluoroalkyl ether sulfonate surfactant is useful for altering surface behavior, typically for lowering surface tension, and can be used in a variety of applications, such as coatings, cleaners, oil fields, and in many other applications involving wetting, leveling, antiblocking, foaming, and the like. The fluoroalkyl ether sulfonate surfactant provides very low surface tension such as less than 24 mN/m.

The present invention further comprises a process for the dispersion polymerization of fluorinated olefin monomer in an aqueous polymerization medium in the presence of a fluoroalkyl ether sulfonate surfactant, which contains a perfluoroalkyl chain of no more than 4 continuous carbons.

The present invention comprises a compound of formula (1)

$$R_f-O-(CXX')_m-(CY_2)_n SO_3 M \qquad (1)$$

wherein
$R_f$ is a $C_1$ to $C_4$ linear or branched perfluoroalkyl group,
X and X' are each independently H or F, provided that at least one of X or X' is F,
each Y is independently H or F,
m is an integer from 1 to 4,
n is an integer from 1 to 2, and
M is H, $NH_4$, Li, Na or K,
provided that when CXX' is CHF or CFH, then n is 2.

Preferred compounds of formula (1) are those wherein $R_f$ is $C_2F_5$ or $C_3F_7$. Also preferred are those compounds of formula (1) wherein m is 2 and n is 2, and wherein M is H or Na.

One particular embodiment of formula (1) wherein X and X' are each F, Y is H, and n is 2, is a fluoroalkyl ether sulfonate surfactant of the following formula:

$$R_f-O-(CF_2)_m-(CH_2)_2 SO_3 M$$

wherein $R_f$, m and M are as defined above for formula (1). Examples of this embodiment include $$CF_3-O-(CF_2)_2-(CH_2)_2 SO_3 M,$$

$$C_2F_5-O-(CF_2)_2-(CH_2)_2 SO_3 M,$$

$$C_3F_7-O-(CF_2)_2-(CH_2)_2 SO_3 M,$$

$C_4F_9-O-(CF_2)_2-(CH_2)_2SO_3M$, and $C_3F_7-O-CF(CF_3)CF_2-(CH_2)_2SO_3M$.

The compounds of the present invention are prepared, for example, according to the following reaction scheme. While this scheme is provided for the example of formula (1) wherein X and X' are each F, m is 2, each Y is H, n is 2, and M is H, it is recognized that analogous reactions are used to make other specific examples of formula (1).

Scheme 1

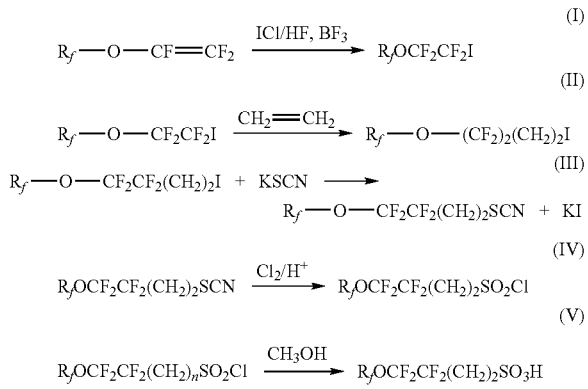

In the first reaction the perfluoroalkyl ether iodide $R_fOCF_2CF_2I$ is made by reaction of a perfluorinated compound which contains a carbon carbon double bond with ICl in HF solvent in the presence of a Lewis acid catalyst. The perfluorinated compounds which contain a carbon carbon double bond are exemplified, but not limited to, $CF_3-O-CF=CF_2$, $C_2F_5-O-CF=CF_2$, $C_3F_7-O-CF=CF_2$, $C_4F_9-O-CF=CF_2$, $C_3F_7-O-C(CF_3)CF_2$, or $C_3F_7-O-CF(CF_3)CF_2-O-CF=CF_2$, and the like. Further details of the process for the preparation the perfluoroalkyl ether iodides is described in U.S. Pat. No. 5,481,028, herein incorporated by reference.

The resulting perfluoroalkyl ether iodide is treated with ethylene by procedures as described in U.S. Pat. No. 3,979,469, to provide the fluoroethyl ethylene iodides $R_fO-(CF_2)_2(CH_2)_2I$ (II). The fluoroethyl iodide is then reacted with potassium thiocynate with trioctylmethylammonium chloride in water to provide a fluoroethyl ethylene thiocyanate $R_f-O-CF_2CF_2(CH_2)_2SCN$ (III). Chlorine gas then is fed into a mixture of the fluoroethyl ethylene thiocyanate (III) and acetic acid. The product obtained is $R_fOCF_2CF_2(CH_2)_nSO_2Cl$ (IV), which is then treated with methanol to provide $R_fOCF_2CF_2(CH_2)_2SO_3H$ (V).

Alternately fluoroalkyl ether sulfonate salts when M is $NH_4$, Li, Na or K are prepared by allowing fluoroethyl ethylene iodides $R_f-O-(CF_2)_2(CH_2)_2I$ (II) to react with corresponding sulfites, such as sodium sulfite in a mixture of ethanol and water.

Another particular embodiment of the compounds of formula (1) of the present invention wherein X' is H, and m and n are each 1, is the fluoroalkyl ether sulfonate surfactant of the following formula:

$R_f-O-CXH-CY_2-SO_3M$ wherein $R_f$, X, Y and M are as defined above for formula (1). These compounds can be made by reacting fluorovinyl ether of the formula $R_f-O-CX=CX_2$ with aqueous sulfite solution adjusted to a pH of from about 4 to about 12 as shown in the equation below:

$R_f-O-CF=CF_2+MHSO_3\rightarrow R_f-O-CHF-CF_2SO_3M$ (VI)

In the making the hydrofluoroalkanesulfonates of this embodiment a suitable vessel, preferably of stainless steel or other corrosion resistant metal, is charged with an aqueous sulfite solution. The solution can be prepared outside the vessel, or made in situ, by charging water and dry ingredients. If it is desired to avoid handling dry ingredients, the sulfite solution can be prepared by adding sulfur dioxide ($SO_2$) to aqueous caustic, preferably sodium or potassium hydroxide. If a sulfite salt, such as sodium or potassium sulfite is the sulfite source, sulfuric acid is a convenient acid for pH adjustment.

After the aqueous sulfite is charged, the vessel is cooled to from about 0° C. to about −40° C., evacuated, and then charged with nitrogen or other inert gas at least once and preferably 2 to 3 times to eliminate oxygen. The vessel is evacuated and then charged with the fluorovinyl ether, closed, and heating is begun. The temperature is raised to about 125° C. and held there with the agitation of the vessel contents for about 2 to 12 hours. At the end of the reaction time, the vessel is cooled to room temperature, vented, and the contents discharged. The contents can be concentrated by removal of water. After water-removal, the solid (crude product) can be further purified by stirring in reagent grade acetone for several hours at room temperature. The product hydrofluoroalkanesulfonate dissolves in acetone, and the inorganic salts, such as residual sulfite salts, do not. The undissolved impurities can be removed by filtration. The acetone solution is then subject to vacuum to remove the acetone. The resulting solid is purified hydrofluoroalkanesulfonate salt. The salt can be converted to the acid by reaction with an acid such as by contact with strong acid crosslinked polystyrene. The corresponding hydrofluoroalkanesulfonate and hydrofluoroalkanesulfonic acid can be represented as a hydrofluoroalkane sulfonate of the formula: $R_fO-CXH-CX_2-SO_3M$. Further details of such a process for the preparation of the said hydrofluoroalkanesulfonates is described in U.S. Patent Application 2006/0276670, herein incorporated by reference.

The compound of formula (1) is a fluoroalkyl ether sulfonate surfactant which lowers surface tension at very low concentration. Such surface tension values in a medium, typically a liquid are less than about 25 milli-newtons per meter, preferably less than about 20 milli-newtons per meter, at a concentration of the surfactant in the medium of less than about 0.2% by weight, and preferably less than 0.1% by weight. The surfactant is characterized by its efficiency in lowering the surface tension at low concentrations by selective adsorption on the interface, which is determined by the amphiphilic nature of the surfactants. The term "amphiphilic" means attraction to two different kinds of media. The surfactants comprise a water-soluble hydrophilic part and a water-insoluble hydrophobic part.

The above compound of formula (1) comprises one hydrophobic part which contains the fluoroalkyl ether group. As a result, the compound is able to lower surface tension at very low concentration. Having the hydrophobic part consisting of $R_f$ group, the compound represented by formula (1) of the present invention exhibits both hydrophobic and oleophobic properties. The compound of formula (1) also comprises a hydrophilic part which contains sulfonic acid, or a salt of the acid. The hydrophilic part provides effective solubility in water media, and therefore the compounds represented by formula (1) of the present invention exhibit surfactant properties.

The compounds of the present invention are distinguished by their exceptional chemical stability in corrosive medium, in particular, very acidic solutions. The compound can be used as antistat in films. The compound is also a very low foaming agent. Such fluoroalkyl ether sulfonate surfactant imparts additional properties. The compound is useful for a formulation based on aggressive (highly acidic, oxidizing, or reducing) media, such as in chrome plating baths. For example, such fluoroalkyl ether sulfonate surfactant of the present invention can be used as a special additive to improve the performance of standby valve-regulated lead acid batteries. As described by Torcheux in "Effect of a special additive on the performance of standby valve-regulated lead acid batteries" Journal of Power Sources Vol. 78, Issues 1-2, Page 147-155 (1999), a polyfluoroalkyl sulfonic acid is used as electrolyte additive to improve the performance of standby VRLA batteries. The fluoroalkyl ether sulfonate surfactant of the present invention has a high stability in sulfuric acid, even at high potentials, and can effectively decrease the electrochemical activity at the electrodes and to limit corrosion and drying out; therefore significantly improving the performance of batteries.

The above compound of formula (1) provides to the medium to which it is added improved surface effects. The improved surface effects include blocking resistance, enhanced hiding power (leveling), spreading, wettability, penetrability, foam inhibition and dispersibility. The improved surface effects by the compounds of the present invention are suitable for many industrial applications including aqueous coatings such as inks, paints, varnishes, and the like. For example, the fluoroalkyl ether sulfonate surfactant of formula (1) provides wetting of the surface of the components to be treated and promotes the formation of a layer of foam on the surface of the chrome plating bath, preventing dangerous chromic acid fume generation. In metal treatment, the fluoroalkyl ether sulfonate surfactant of formula (1) can be used for cleaning, decaling and picking.

The present invention further comprises a process comprising polymerizing at least one fluorinated olefin monomer in an aqueous medium in the presence of a compound of the formula (1A):

$$R_f-O-(CXX')_m-(CY_2)_n SO_3 M \quad (1A)$$

wherein $R_f$ is a $C_1$ to $C_4$ linear or branched perfluoroalkyl group,

X and X' are each independently H or F, provided that at least one of X or X' is F, each Y is independently H or F, m is an integer from 1 to 4, n is an integer from 1 to 2, and M is H, $NH_4$, Li, Na or K, to form an aqueous dispersion of fluoropolymer.

One of the advantages of using the surfactants comprising the fluoroalkyl ether sulfonate surfactant of the present invention in a dispersion polymerization processes is to achieve equally stable dispersions and increased polymerization rate while using reduced fluorine content. Further the reduced fluorine content of the surfactant increases the "fluorine efficiency". By the term "fluorine efficiency" as used herein is meant the ability to use a minimum amount of fluorosurfactants and use a lower level of fluorine to obtain the desired dispersion of polymers.

In accordance with the invention, the fluoroalkyl ether sulfonic acid or salt of formula (I) is preferably dispersed adequately in aqueous medium to function effectively as a polymerization agent. "Dispersed" as used in this application refers to either dissolved in cases in which the fluoroalkyl ether sulfonic acid or salt surfactant is soluble in the aqueous medium, or dispersed in cases in which the fluoroalkyl ether sulfonic acid or salt surfactant is not fully soluble and is present in very small particles, for example about 1 nm to about 1 micrometer particle size distribution, in the aqueous medium. Similarly, "dispersing" as used in this application refers to either dissolving or dispersing the fluoroalkyl ether sulfonic acid or salt surfactant so that it is dispersed as defined above. Preferably, the fluoroalkyl ether sulfonic acid or salt surfactant is dispersed sufficiently so that the polymerization medium containing the fluoroalkyl ether sulfonic acid or salt surfactant appears water clear or nearly water clear.

Preferably, the total amount of polymerization agent used in a preferred process in accordance with the invention is from about 5 to about 10,000 micrograms/g based on the weight of water in the aqueous medium, more preferably from about 5 to about 3000 micrograms/g based on the weight of water in the aqueous medium. Even more preferably, the total amount of polymerization agent used is from about 0.01% by weight to about 10% by weight based on the weight of water in the aqueous medium, still more preferably from about 0.05% to about 3% by weight, more preferably from about 0.05% to about 3% based on the weight of water in the aqueous medium.

At least a portion of the polymerization agent is preferably added to the polymerization prior to the beginning of the polymerization. If added subsequently, a variety of modes of addition for the polymerization agent can be used including continuously throughout the polymerization or in doses or intervals at predetermined times during the polymerization. In accordance with one embodiment of the invention, substantially all of the polymerization agent is added to the aqueous medium prior to the start of polymerization, preferably prior to initiator addition.

In accordance with a preferred embodiment of the invention the polymerization agent used in the practice of this invention is preferably substantially free of perfluoropolyether oil (i.e., perfluoropolyethers having neutral, nonionic, preferably fluorine or hydrogen, end groups). Substantially free of perfluoropolyether oils means that aqueous polymerization medium contains no more than about 10 micrograms/g of such oils based on water. Thus, the fluoropolymer dispersion preferably produced has high purity and preferably is substantially free of perfluoropolyether oils. Moreover, in a preferred process, the polymerization medium is substantially free of fluoropolymer seed at the start of polymerization (kick-off). In this preferred form of the invention, fluoropolymer seed, i.e., separately polymerized small fluoropolymer particles in dispersion form, is not added prior to the start of polymerization.

It has been found that the polymerization agent of formula (1) used in the present invention can produce fluoropolymers and provide low levels of undispersed polymer (referred to as coagulum) substantially equivalent to those made using the typical perfluoroalkane carboxylic acid surfactants and at high dispersion solids concentrations.

The polymerization process can be carried out as a batch, semi-batch or continuous process in a pressurized reactor. In a batch process, all of the ingredients are added to the polymerization reactor at the beginning of the run and are allowed to react to completion before discharging the vessel. In a semibatch process, one or more ingredients (such as monomers, initiator, surfactant, etc.) are added to the vessel over the course of the reaction following the initial precharging of the reactor. At the completion of a semibatch process, the contents are discharged from the vessel. In a continuous process, the reactor is precharged with a predetermined composition and then monomers, surfactants, initiators and water are continuously fed into the reactor while an equivalent volume of reaction goods are continuously removed from the reactor, resulting in a controlled volume of reacting goods inside the reactor. Following this start-up procedure, a continuous process can run indefinitely as long as feed material continues to be metered into the reactor and product goods are removed. When shut-down is desired, the feeds to the reactor can be stopped and the reactor discharged.

In one preferred embodiment of the invention, the polymerization process is carried out as a batch process in a pressurized reactor. Suitable vertical or horizontal reactors for carrying out the process of the invention are equipped with stirrers for the aqueous medium. The reactor provides sufficient contact of gas phase monomers such as tetrafluoroethylene (TFE) for desirable reaction rates and uniform incorporation of comonomers if employed. The reactor preferably includes a cooling jacket surrounding the reactor so that the reaction temperature is conveniently controlled by circulation of a controlled temperature heat exchange medium.

In a typical process, the reactor is first charged with deionized and deaerated water of the polymerization medium, and the perfluoroalkyl ether acid or salt surfactant of formula (I) is dispersed in the medium. The dispersing of the fluoroalkyl ether sulfonic acid or salt surfactant is as discussed above. At least a portion of the polymerization agent is preferably added to the polymerization prior to the beginning of the polymerization. If added subsequently, a variety of modes of addition for the polymerization agent can be used including continuously throughout the polymerization or in doses or intervals at predetermined times during the polymerization.

For polytetrafluoroethylene (PTFE) homopolymer and modified polytetrafluoroethylene (PTFE), paraffin wax as stabilizer is often added. A suitable procedure for polytetrafluoroethylene (PTFE) homopolymer and modified polytetrafluoroethylene (PTFE) includes first pressurizing the reactor with tetrafluoroethylene (TFE). If used, the comonomer such as hexafluoropropylene (HFP) or perfluoro(alkyl vinyl ether) (PAVE) is then added. A free-radical initiator solution such as ammonium persulfate solution is then added. For polytetrafluoroethylene (PTFE) homopolymer and modified polytetrafluoroethylene (PTFE), a second initiator which is a source of succinic acid such as disuccinyl peroxide may be present in the initiator solution to reduce coagulum. Alternatively, a redox initiator system such as potassium permanganate/oxalic acid is used. The temperature is increased and, once polymerization begins, additional tetrafluoroethylene (TFE) is added to maintain the pressure. The beginning of polymerization is referred to as kick-off and is defined as the point at which gaseous monomer feed pressure is observed to drop substantially, for example, about 10 psi (about 70 kPa). Comonomer and/or chain transfer agent can also be added as the polymerization proceeds. For some polymerizations, additional monomers, initiator and or polymerization agent may be added during the polymerization.

After batch completion (typically several hours) when the desired amount of polymer or solids content has been achieved, the feeds are stopped, the reactor is vented and purged with nitrogen, and the raw dispersion in the vessel is transferred to a cooling vessel.

The solids content of the dispersion upon completion of polymerization can be varied depending upon the intended use for the dispersion. For example, the process of the invention can be employed to produce a "seed" dispersion with low solids content, e.g., less than 10% by weight, which is employed as "seed" for a subsequent polymerization process to a higher solids level. In other processes, the solids content of fluoropolymer dispersion produced by the process of the invention is preferably at least about 10% by weight. More preferably, the fluoropolymer solids content is at least about 20% by weight. A preferred range for fluoropolymer solids content produced by the process is about 14% by weight to about 65% by weight, even more preferably about 20% by weight to about 55% by weight, most preferably, about 35% by weight to about 55% by weight.

In a preferred process of the invention, polymerizing produces less that about 10% by weight, more preferably less than 3% by weight, even more preferably less than 1% by weight, most preferably less that about 0.5% by weight undispersed fluoropolymer (coagulum) based on the total weight of fluoropolymer produced.

The as-polymerized dispersion can be stabilized with anionic, cationic, or nonionic surfactant for certain uses. Typically however, the as-polymerized dispersion is transferred to a dispersion concentration operation which produces concentrated dispersions stabilized typically with nonionic surfactants by known methods. Solids contents of concentrated dispersion are typically about 35 to about 70% by weight. Certain grades of polytetrafluoroethylene (PTFE) dispersion are made for the production of fine powder. For this use, the dispersion is coagulated, the aqueous medium is removed and the polytetrafluoroethylene (PTFE) is dried to produce fine powder.

The dispersion polymerization of melt-processible copolymers is similar except that comonomer in significant quantity is added to the batch initially and/or introduced during polymerization. Chain transfer agents are typically used in significant amounts to decrease molecular weight to increase melt flow rate. The same dispersion concentration operation can be used to produce stabilized concentrated dispersions. Alternatively, for melt-processible fluoropolymers used as molding resin, the dispersion is coagulated and the aqueous medium is removed. The fluoropolymer is dried, then processed into a convenient form such as flake, chip or pellet for use in subsequent melt-processing operations.

The process of the invention can also be carried out as a semi-batch or as a continuous process in a pressurized reactor. These processes are especially suitable for the manufacture of fluorocarbon elastomers. In the semi-batch emulsion polymerization process of this invention, a gaseous monomer mixture of a desired composition (initial monomer charge) is introduced into a reactor which contains an aqueous medium precharge. Other ingredients, such as initiators, chain transfer agents, buffers, bases, and surfactants can be added with the water in the precharge, and also during the polymerization reaction. Additional monomers at concentrations appropriate to the final polymer composition desired, are added during the polymerization reaction at a rate needed to maintain system pressure. Polymerization times in the range of from about 2 to about 30 hours are typically employed in the semi-batch polymerization process. In a continuous process, the reactor is completely filled with aqueous medium so that there is no vapor space. Gaseous monomers and solutions of other ingredients such as water-soluble monomers, chain transfer agents, buffer, bases, polymerization initiator, surfactant, etc., are fed to the reactor in separate streams at a constant rate. Feed rates are controlled so that the average polymer residence time in the reactor is generally between 0.2 to about 4 hours, depending on monomer reactivity. For both types of processes, the polymerization temperature is maintained in the range of from about 25° to about 130° C., preferably in the range of from about 50° C. to about 100° C. for semi-batch operation, and from about 70° C. to about 120° C. for continuous. The polymerization pressure is controlled in the range of from about 0.5 to about 10 MPa, preferably from about 1 to about 6.2 MPa. The amount of fluoropolymer formed is approximately equal to the amount of incremental feed charged, and is in the range of from about 10 to about 30 parts by weight of fluoropolymer per 100 parts by weight of aqueous emulsion, preferably in the range of from about 20 to about 30 parts by weight of the fluoropolymer.

Polymerization in accordance with the invention employs free radical initiators capable of generating radicals under the conditions of polymerization. As is well known in the art, initiators for use in accordance with the invention are selected based on the type of fluoropolymer and the desired properties to be obtained, e.g., end group type, molecular weight, etc. For some fluoropolymers such as melt-processible tetrafluoroethylene (TFE) copolymers, water-soluble salts of inorganic peracids are employed which produce anionic end groups in the polymer. Preferred initiators of this type have a relatively long half-life, preferably persulfate salts, e.g., ammonium persulfate or potassium persulfate. To shorten the half-life of persulfate initiators, reducing agents such as ammonium bisulfite or sodium metabisulfite, with or without metal catalyst salts such as Fe, can be used. Preferred persulfate initiators are substantially free of metal ions and most preferably are ammonium salts.

For the production of polytetrafluoroethylene (PTFE) or modified polytetrafluoroethylene (PTFE) dispersions for dispersion end uses, small amounts of short chain dicarboxylic acids such as succinic acid or initiators that produce succinic acid such as disuccinic acid peroxide (DSP) are preferably also added in addition to the relatively long half-life initiators such as persulfate salts. Such short chain dicarboxylic acids are typically beneficial in reducing undispersed polymer (coagulum). For the production of polytetrafluoroethylene (PTFE) dispersion for the manufacture of fine powder, a redox initiator system such as potassium permanganate/oxalic acid is often used.

The initiator is added to the aqueous polymerization medium in an amount sufficient to initiate and maintain the polymerization reaction at a desired reaction rate. At least a portion of the initiator is preferably added at the beginning of the polymerization. A variety of modes of addition may be used including continuously throughout the polymerization, or in doses or intervals at predetermined times during the polymerization. A particularly preferred mode of operation is for initiator to be precharged to the reactor and additional initiator to be continuously fed into the reactor as the polymerization proceeds. Preferably, total amounts of ammonium persulfate and/or potassium persulfate employed during the course of polymerization are about 25 micrograms/g to about 250 micrograms/g based on the weight of the aqueous medium. Other types of initiators, for example, potassium permanganate/oxalic acid initiators, can be employed in amounts and in accordance with procedures as known in the art.

Chain-transfer agents can be used in a process in accordance with the invention for the polymerization of some types of polymers, e.g., for melt-processible tetrafluoroethylene (TFE) copolymers, to decrease molecular weight for the purposes of controlling melt viscosity. Chain transfer agents useful for this purpose are well-known for use in the polymerization of fluorinated monomers. Preferred chain transfer agents include hydrogen, aliphatic hydrocarbons, halocarbons, hydrohalocarbons or alcohols having 1 to 20 carbon atoms, more preferably 1 to 8 carbon atoms. Representative examples of such chain transfer agents are alkanes such as ethane, chloroform, 1,4-diiodoperfluorobutane and methanol.

The amount of a chain transfer agent and the mode of addition depend on the activity of the particular chain transfer agent and on the desired molecular weight of the polymer product. A variety of modes of addition can be used including a single addition before the start of polymerization, continuously throughout the polymerization, or in doses or intervals at predetermined times during the polymerization. The amount of chain train transfer agent supplied to the polymerization reactor is preferably about 0.005 to about 5% by weight, more preferably from about 0.01 to about 2% by weight based upon the weight of the resulting fluoropolymer.

In accordance with the invention, the present invention provides a process as one of the embodiments of the invention comprising polymerizing olefin fluoromonomers in aqueous medium containing the fluoroalkyl ether sulfonate surfactants of formula (1). The fluoroalkyl ether sulfonate surfactants of formula (1) are used in the process of the aqueous dispersion polymerization of olefin fluoromonomers. Water-soluble initiator is generally used in amount of from about 2 to about 500 micrograms/g based on the weight of water present. Examples of such initiators include ammonium persulfate, potassium persulfate, permanganate/oxalic acid, and disuccinic acid peroxide. The polymerization can be carried out by charging the polymerization reactor with water, surfactant, olefin fluoromonomers, and optionally chain transfer agent, agitating the contents of the reactor, and heat the reactor to the desired polymerization temperature, e.g., from about 25° to about 110° C.

The amount of the fluoroalkyl ether sulfonic acid or salt surfactant of formula (I) used in the process of the invention mentioned above is within known ranges, for example, from about 0.01% by weight to about 10% by weight, preferably from about 0.05 to about 3% by weight, more preferably from about 0.05 to about 1.0% by weight, based on the water used in the polymerization. The concentration of surfactant that can be employed in the polymerization process of the present invention can be above or below the critical micelle concentration (c.m.c.) of the surfactant.

The process of the present invention provides a dispersion of fluoropolymers as the result of the aqueous dispersion polymerization of olefin fluoromonomers described above.

Fluoropolymer dispersions formed by this invention are comprised of particles of fluoropolymer made from at least one fluorinated monomer, i.e., wherein at least one of the monomers contains fluorine, preferably an olefinic monomer with at least one fluorine or a perfluoroalkyl group attached to a doubly-bonded carbon. The fluorinated monomer used in the process of this invention is preferably independently selected from the group consisting of tetrafluoroethylene (TFE), hexafluoropropylene (HFP), chlorotrifluoroethylene (CTFE), trifluoroethylene, hexafluoroisobutylene, perfluoroalkyl ethylene, fluorovinyl ethers, vinyl fluoride (VF), vinylidene fluoride (VF2), perfluoro-2,2-dimethyl-1,3-dioxole (PDD), perfluoro-2-methylene-4-methyl-1,3-dioxolane (PMD), perfluoro(allyl vinyl ether) and perfluoro(butenyl vinyl ether). A preferred perfluoroalkyl ethylene monomer is perfluorobutyl ethylene (PFBE). Preferred fluorovinyl ethers include perfluoro(alkyl vinyl ether) monomers (PAVE) such as perfluoro(propyl vinyl ether) (PPVE), perfluoro(ethyl vinyl ether) (PEVE), and perfluoro(methyl vinyl ether) (PMVE). Non-fluorinated olefinic comonomers such as ethylene and propylene can be copolymerized with fluorinated monomers.

Fluorovinyl ethers also include those useful for introducing functionality into fluoropolymers. These include $CF_2=CF-(O-CF_2CFR_f)_a-O-CF_2CFR'_fSO_2F$, wherein $R_f$ and $R'_f$ are independently selected from F, Cl or a perfluorinated alkyl group having 1 to 10 carbon atoms, a=0, 1 or 2. Polymers of this type are disclosed in U.S. Pat. No. 3,282,875 ($CF_2=CF-O-CF_2CF(CF_3)-O-CF_2CF_2SO_2F$, perfluoro(3,6-dioxa-4-methyl-7-octenesulfonyl fluoride)), and in U.S. Pat. Nos. 4,358,545 and 4,940,525 ($CF_2=CF-O-CF_2CF_2SO_2F$). Another example is $CF_2=CF-O-CF_2-CF(CF_3)-O-CF_2CF_2CO_2CH_3$, methyl ester of perfluoro (4,7-dioxa-5-methyl-8-nonenecarboxylic acid), disclosed in U.S. Pat. No. 4,552,631. Similar fluorovinyl ethers with functionality of nitrile, cyanate, carbamate, and phosphate are disclosed in U.S. Pat. Nos. 5,637,748; 6,300,445; and 6,177,196.

The invention is especially useful when producing dispersions of polytetrafluoroethylene (PTFE) including modified polytetrafluoroethylene (modified PTFE). PTFE and modified PTFE typically have a melt creep viscosity of at least about $1\times10^8$ Pa·s and, with such high melt viscosity, the polymer does not flow significantly in the molten state and therefore is not a melt-processible polymer.

Polytetrafluoroethylene (PTFE) refers to the polymerized tetrafluoroethylene by itself without any significant comonomer present. Modified PTFE refers to copolymers of tetrafluoroethylene (TFE) with such small concentrations of comonomer that the melting point of the resultant polymer is not substantially reduced below that of PTFE. The concentration of such comonomer is preferably less than 1% by weight, more preferably less than 0.5% by weight. A minimum amount of at least about 0.05% by weight is preferably used to have significant effect. The modified PTFE contains a small amount of comonomer modifier which improves film forming capability during baking (fusing), such as perfluoroolefin, notably hexafluoropropylene (HFP) or perfluoro (alkyl vinyl ether) (PAVE), where the alkyl group contains 1 to 5 carbon atoms, with perfluoro(ethyl vinyl ether) (PEVE) and perfluoro(propyl vinyl ether) (PPVE) being preferred. Chlorotrifluoroethylene (CTFE), perfluorobutyl ethylene (PFBE), or other monomer that introduces bulky side groups into the molecule are also included.

The invention is especially useful when producing dispersions of melt-processible fluoropolymers. By melt-processible, it is meant that the polymer can be processed in the molten state (i.e., fabricated from the melt into shaped articles such as films, fibers, and tubes etc. that exhibit sufficient strength and toughness to be useful for their intended purpose) using conventional processing equipment such as extruders and injection molding machines. Examples of such melt-processible fluoropolymers include homopolymers such as polychlorotrifluoroethylene or copolymers of tetrafluoroethylene (TFE) and at least one fluorinated copolymerizable monomer (comonomer) present in the polymer usually in sufficient amount to reduce the melting point of the copolymer substantially below that of tetrafluoroethylene (TFE) homopolymer, polytetrafluoroethylene (PTFE), e.g., to a melting temperature no greater than 315° C.

A melt-processible tetrafluoroethylene (TFE) copolymer typically incorporates an amount of comonomer into the copolymer in order to provide a copolymer which has a melt flow rate (MFR) of about 1-100 g/10 min as measured according to ASTM D-1238 at the temperature which is standard for the specific copolymer. Preferably, the melt viscosity is at least about $10^2$ Pa·s, more preferably, will range from about $10^2$ Pa·s to about $10^6$ Pa·s, most preferably about $10^3$ to about $10^5$ Pa·s measured at 372° C. by the method of ASTM D-1238 modified as described in U.S. Pat. No. 4,380,618. Additional melt-processible fluoropolymers are the copolymers of ethylene (E) or propylene (P) with tetrafluoroethylene (TFE) or chlorotrifluoroethylene (CTFE), notably ethylene tetrafluoroethylene (ETFE), ethylene chlorotrifluoroethylene (ECTFE) and propylene chlorotrifluoroethylene (PCTFE). A preferred melt-processible copolymer for use in the practice of the present invention comprises at least about 40-98 mol % tetrafluoroethylene units and about 2-60 mol % of at least one other monomer. Preferred comonomers with tetrafluoroethylene (TFE) are perfluoroolefin having 3 to 8 carbon atoms, such as hexafluoropropylene (HFP), and/or perfluoro(alkyl vinyl ether) (PAVE) in which the linear or branched alkyl group contains 1 to 5 carbon atoms. Preferred PAVE monomers are those in which the alkyl group contains 1, 2, 3 or 4 carbon atoms, and the copolymer can be made using several PAVE monomers.

Preferred tetrafluoroethylene (TFE) copolymers include 1) tetrafluoroethylene/hexafluoropropylene (TFE/HFP) copolymer; 2) tetrafluoroethylene/perfluoro(alkyl vinyl ether) (TFE/PAVE) copolymer; 3) tetrafluoroethylene/hexafluoro propylene/perfluoro (alkyl vinyl ether) (TFE/HFP/PAVE) copolymer wherein the perfluoro (alkyl vinyl ether) is perfluoro(ethyl vinyl ether) or perfluoro(propyl vinyl ether); 4) melt processible tetrafluoroethylene/perfluoro(methyl vinyl ether)/perfluoro (alkyl vinyl ether) (TFE/PMVE/PAVE) copolymer wherein the alkyl group of perfluoro (alkyl vinyl ether) (PAVE) has at least two carbon atoms); and 5) tetrafluoroethylene/hexafluoropropylene/vinylidene fluoride copolymer (TFE/HFP/VF2)).

Further useful polymers are film forming polymers of polyvinylidene fluoride (PVDF) and copolymers of vinylidene fluoride as well as polyvinyl fluoride (PVF) and copolymers of vinyl fluoride.

The invention is also useful when producing dispersions of fluorocarbon elastomers. These elastomers typically have a glass transition temperature below 25° C. and exhibit little or no crystallinity at room temperature. Fluorocarbon elastomer copolymers made by the process of this invention typically contain 25 to 70% by weight, based on total weight of the fluorocarbon elastomer, of copolymerized units of a first fluorinated monomer which may be vinylidene fluoride (VF2) or tetrafluoroethylene (TFE). The remaining units in the fluorocarbon elastomers are comprised of one or more additional copolymerized monomers, different from said first monomer, selected from the group consisting of fluorinated monomers, hydrocarbon olefins and mixtures thereof. Fluorocarbon elastomers prepared by the process of the present invention may also, optionally, comprise units of one or more cure site monomers. When present, copolymerized cure site monomers are typically at a level of 0.05 to 7% by weight, based on total weight of fluorocarbon elastomer. Examples of suitable cure site monomers include: i) bromine-, iodine-, or chlorine-containing fluorinated olefins or fluorinated vinyl ethers; ii) nitrile group-containing fluorinated olefins or fluorinated vinyl ethers; iii) perfluoro(2-phenoxypropyl vinyl ether); and iv) non-conjugated dienes.

Preferred tetrafluoroethylene (TFE) based fluorocarbon elastomer copolymers include tetrafluoroethylene/perfluoro (methyl vinyl ether) (TFE/PMVE); tetrafluoroethylene/perfluoro(methyl vinyl ether)/ethylene (TFE/PMVE/E); tetrafluoroethylene/propylene (TFE/P); and tetrafluoroethylene/propylene/vinylidene fluoride (TFE/P/VF2). Preferred vinylidene fluoride (VF2) based fluorocarbon elastomer copolymers include vinylidene fluoride/hexafluoropropylene (VF2/HFP); vinylidene fluoride/hexafluoropropylene/tetrafluoroethylene (VF2/HFP/TFE);

and vinylidene fluoride/perfluoro(methyl vinyl ether)/tetrafluoroethylene (VF2/PMVE/TFE). Any of these elastomer copolymers may further comprise units of cure site monomer.

The present invention further comprises a method of altering the surface behavior of a liquid comprising adding to the liquid the composition of a compound of formula (1A):

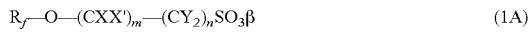

$$R_f\text{—}O\text{—}(CXX')_m\text{—}(CY_2)_n SO_3\beta \qquad (1A)$$

wherein
$R_f$ is a $C_1$ to $C_4$ linear or branched perfluoroalkyl group,
X and X' are each independently H or F, provided that at least one of X or X' is F,
each Y is independently H or F,
m is an integer from 1 to 4,
n is an integer from 1 to 2, and
M is H, $NH_4$, Li, Na or K.

The method of altering the surface behavior of a liquid of the present invention is useful in a wide variety of applications. The surfactants of formula (1A) are typically used by simply blending with or adding to water, aqueous solutions, and aqueous emulsions. The surfactants of formulae (1A) typically lower surface and interfacial tensions and provide low critical micelle concentrations. Examples of surface behavior alteration include improvements in the properties of wetting, penetration, spreading, leveling, flowing, emulsifying, stabilization of dispersions in liquids, repellency, releasing, lubricating, etching, and bonding.

Examples of such applications where low surface tension is required include coating compositions and aqueous and non-aqueous cleaning products, each for glass, wood, metal, brick, concrete, cement, natural and synthetic stone, tile, synthetic flooring, laminates, paper, textile materials, linoleum and other plastics, resins, natural and synthetic rubbers, fibers and fabrics, and paints; polymers; and waxes, finishes, leveling and gloss agents for floors, furniture, shoes, inks, and automotive care. Wetting agent applications include wetting agents for compositions containing herbicides, fungicides, weed killers, hormone growth regulators, parasiticides, insecticides, germicides, bactericides, nematocides, microbiocides, defoliants or fertilizers, therapeutic agents, antimicrobials, fluorochemical blood substitutes, textile treatment baths, and fiber spin finishes. Applications in personal care products include shampoos, conditioners, creme rinses, cosmetic products for the skin (such as therapeutic or protective creams and lotions, oil and water repellent cosmetic powders, deodorants and antiperspirants), nail polish, lipstick, and toothpaste. Further applications include fabric care products (such as stain pretreatments and/or stain removers for clothing, carpets and upholstery), and laundry detergents. Other applications include rinse-aids (for car washes and in automatic dishwashers), for oil well treatments (including drilling muds and additives to improve tertiary oil well recovery), extreme pressure lubricants, lubricating cutting oil to improve penetration times, writing inks, printing inks, photography developer solutions, emulsions for fighting forest fires, dry chemical fire extinguishing agents, aerosol-type fire extinguishers, thickening agents to form gels for solidifying or encapsulating medical waste, photoresists, developers, cleaning solutions, etching compositions, developers, polishers, and resist inks in the manufacturing, processing, and handling of semiconductors and electronics. The surfactants of formula (1A) can be incorporated into products that function as antifogging agents for glass surfaces and photography films, and as antistatic agents for magnetic tapes, phonograph records, floppy disks, disk drives, rubber compositions, PVC, polyester film, and photography films, and as surface treatments for optical elements (such as glass, plastic, or ceramics). Other applications are in emulsifying agents, foaming agents, release agents, repellency agents, flow modifiers, film evaporation inhibitors, wetting agents, penetrating agents, cleaners, grinding agents, electroplating agents, corrosion inhibitors, soldering agents, dispersion aids, microbial agents, pulping aids, rinsing aids, polishing agents, drying agents, antistatic agents, antiblocking agents, bonding agents, and oil field chemicals.

The compounds of formula (1A) are also useful as foam control agents in polyurethane foams, spray-on oven cleaners, foamed kitchen and bathroom cleansers and disinfectants, aerosol shaving foams, and in textile treatment baths. The surfactants of formula (1A) are useful as emulsifying agents for polymerization, particularly of fluoromonomers, as latex stabilizers, as mold release agents for silicones, photoemulsion stabilizers, inorganic particles, and pigments. Such fluorosurfactants are also useful for supercritical carbon dioxide emulsions and dispersion of nanoparticles or pigments in water.

A low concentration of less than about 0.1%, preferably less than about 0.01% by weight of a compound of formulae (1A) in the liquid is effective. Consequently, the surfactants of formulae (1A) are useful in a wide variety of end use applications. In particular the surfactants of formula (1A) are useful to provide exceptional chemical stability in aggressive or corrosive media, in particular very acidic solutions. Thus the surfactants of formula (1A) impart properties that prove useful in formulations based on highly acidic, oxidizing, or reducing media. This stability is provided while using shorter perfluoroalkyl groups, thus providing fluorine efficiency.

MATERIALS AND TEST METHODS

The following materials and test methods were used in the examples herein.

Materials

Tetrafluoroethylene was obtained from E. I. du Pont de Nemours and Company, Wilmington, Del. Olefins were commercial grade materials and were used as obtained from E. I. du Pont de Nemours and Company, Wilmington, Del. The vinylidene fluoride was obtained from Solvay Solexus, Inc., West Deptford. N.J. Other reagents were commercially available, for example, from Aldrich Chemical Co., Milwaukee, Wis. The initiator, ammonium persulfate, was purchased from Sigma-Aldrich Corporation, St. Louis, Mo.

Test Methods

Test Method 1—Surface Tension Measurement

Surface tension was measured using a Kruess Tensiometer, K11 Version 2.501 in accordance with instructions with the equipment. The Wilhelmy Plate method was used. A vertical plate of known perimeter was attached to a balance, and the force due to wetting was measured. Ten replicates were tested of each dilution, and the following machine settings were used: Method: Plate Method SFT; Interval: 1.0 s; Wetted length: 40.2 mm; Reading limit: 10; Min Standard Deviation: 2 dynes/cm; Gr. Acc.: 9.80665 m/s$^2$.

Test Method 2—Comonomer Content

Comonomer content perfluoro(propyl vinyl ether) (PPVE) was measured by FTIR according to the method disclosed in U.S. Pat. No. 4,743,658, col. 5, lines 9-23 as follows. The PPVE content was determined by infrared spectroscopy. The ratio of absorbance at 10.07 micrometers to that at 4.25 micrometers was determined under a nitrogen atmosphere using films approximately 0.05 mm thick. The films were compression molded at 350° C., then immediately quenched in ice water. This absorbance ratio was then used to determine percent PPVE by means of a calibration curve established with reference films of known PPVE content. F19 NMR was used as the primary standard for calibrating the reference films.

Test Method 3—Particle Size

Particle size, i.e., raw dispersion particle size (RDPS) was determined by laser fraction techniques that measure the particle size distributions (PSD) of materials using a Microtrac Ultrafine Particle Analyzer (UPA). The UPA uses dynamic light scattering principle for measuring PSD with size range of 0.003 micron to 6.54 micron. The samples were analyzed after collecting the background with water. The measurements were repeated three times and averaged.

Test Method 4—Coagulum

Dry coagulum amount was measured by physically collecting the wet polymer that coagulated during the course of the polymerization, and drying the coagulum overnight at 80° C. at a vacuum of 30 mm Hg (4 kPa). The dried coagulum was weighed to determine the percentage present based on the weight of total fluoropolymer produced.

EXAMPLES

Example 1

$C_3F_7OCF_2CF_2I$ (100 g, 0.24 mol) and benzoyl peroxide (3 g) were charged to a pressure vessel under nitrogen. A series of three vacuum/nitrogen gas sequences was then executed at −50° C. and ethylene (18 g, 0.64 mol) was introduced. The vessel was heated for 24 hour at 110° C. The autoclave was cooled to 0° C. and opened after degassing. Then the product was collected in a bottle. The product was distilled giving 80 g of $C_3F_7OCF_2CF_2CH_2CH_2I$ in 80% yield. The boiling point was 56~60° C. at 25 mm Hg (3333 Pa).

Potassium thiocynate (21.34 g, 0.22 mol) was added to the mixture of $C_3F_7OCF_2CF_2CH_2CH_2I$ (50 g, 0.11 mol) and trioctylmethylammonium chloride (0.2222 g) in 50 g of water. The reaction was heated overnight at 90° C. After phase separation, the product $C_3F_7OCF_2CF_2CH_2CH_2SCN$ was distilled as a colorless liquid (32 g, 78%). The compound can be characterized by: b.p. 83~85° C./2.3 torr; $^1H$ NMR (CDCl$_3$, 400 MHz) δ 3.10~3.07 (2H, m), 2.58~2.46 (2H, m); $^{19}F$ NMR (CDCl$_3$, 373 Hz) δ −81.71 (3F, t, J=7.5 Hz), −84.84~−84.97 (2F, m), −87.96~−88.03 (2F, m), −118.29 (2F, t, J=17.0 Hz), −130.29 (2F, s); MS: 372 (M$^+$).

Chlorine gas (132 g, 1.86 mol) and water (47 g, 2.6 mol) were fed into the mixture of $C_3F_7OCF_2CF_2CH_2CH_2SCN$ (231 g, 0.62 mol) and acetic acid (130 g, 2.17 mol) over 10 hours at 45~50° C. in an autoclave. A further 10 g of chlorine was added over 3 hours at 45° C. and heated at this temperature for 1 hour. The product from PRL was heated in a flask with a stir bar at 70° C. and 149 mL of hot water (70° C.) was added. The organic layer was separated, followed by adding of toluene (125 g). The product in toluene was washed with 3.5% solution of brine (149 mL) at 70° C. twice. After the second wash, a Dean-Stark strap was set up to strip off water. The final product was 70% of $C_3F_7OCF_2CF_2CH_2CH_2SO_2Cl$ (228 g, 90%) by weight in toluene.

$C_3F_7OCF_2CF_2CH_2CH_2SO_2Cl$ (10 g, 0.0242 mol, 66.8% in toluene) was added dropwise to methanol (10 g, 0.313 mol) at 70° C. After the reaction mixture was reflux overnight, methanol and toluene were distilled off. The final product $C_3F_7OCF_2CF_2CH_2CH_2SO_3H$ (9.3 g, 97.5%) was diluted with 70° C. deionized water until it is 30% active. The compound was characterized by: $^1H$ NMR (D$_2$O, 400 MHz) δ 2.99~2.91 (2H, m), 2.49~2.31 (2H, m); $^{19}F$ NMR (D$_2$O, 377 MHz) δ −82.74 (2F, t, J=7.1 Hz), −85.65~85.81 (2F, m), −8.29~88.47 (2F, m), −118.62 (3F, t, J=18.9 Hz), −131.23 (2F, s). The product was added to water and tested for surface tension according to the Test Method 1. Results are in Table 1.

Comparative Example A

The procedure of the above was employed, but using as the fluorchemical a perfluoroalkylethyl alcohol of the formula $F(CF_2)_6CH_2CH_2OH$. The product was added to water and tested for surface tension according to the Test Method 1. Results are in Table 1.

TABLE 1

| | Surface Tension Measurement | | | | | | | |
|---|---|---|---|---|---|---|---|---|
| Example* | 0.001% | 0.005% | 0.010% | 0.050% | 0.100% | 0.200% | 0.500% | 1.00% |
| Example 1 | 72.4 | 68.4 | 65.3 | 45.9 | 34.2 | 24.3 | 18.7 | 15.5 |
| Comparative Example A | 72.5 | 68.4 | 64.4 | 50.6 | 32.1 | 27.4 | 22.1 | 22.8 |

*Example was added to deionized water by weight based on solids of the additive in deionized water; Standard Deviation < 1 dynes/cm; Temperature 23° C. Normal surface tension of deionized water is 72 dyne/cm.

The data in Table 1 shows that when the above fluorosulfonic acid surfactant was added at a specified rate, the surface tension of each aqueous solution was reduced significantly. Example 1 showed better surface tension reduction as the concentration increased compared to Comparative Example A.

Example 2

$C_3F_7OCF_2CF_2I$ (100 g, 0.24 mol) and benzoyl peroxide (3 g) were charged to a pressure vessel under nitrogen. A series of three vacuum/nitrogen gas sequences was then executed at −50° C. and ethylene (18 g, 0.64 mol) was introduced. The vessel was heated for 24 hour at 110° C. The autoclave was cooled to 0° C. and opened after degassing. Then the product was collected in a bottle. The product was distilled giving 80 g of $C_3F_7OCF_2CF_2CH_2CH_2I$ in 80% yield. The boiling point was 56~60° C. at 25 mm Hg (3333 Pa).

$C_3F_7OCF_2CF_2CH_2CH_2I$ (220 g, 0.5 mol) was added to the mixture of ethanol (250 mL) and water (250 mL). Sodium sulfite (126 g, 1 mol) was added, followed by 15 g copper. The reaction mixture was stirred vigorously under reflux for a week. 500 mL water was added and filtered at 75° C. The filtrate was cooled and the product $C_3F_7OCF_2CF_2CH_2CH_2SO_3Na$ was collected by filtration as white solid (86 g, 41.35%). The compound was characterized by: $^1H$ NMR (CDCl$_3$, 400 MHz) δ 3.19~3.15 (2H, m), 2.69~2.56 (2H, m); $^{19}F$ NMR (CDCl$_3$, 373 Hz) δ −81.58 (3F, t, J=7.0 Hz), −84.78~84.92 (2F, m), −88.15 (2F, t, J=13.3 Hz), −117.80 (2F, t, J=18 Hz), −130.19 (2F, s). The product was added to water and tested for surface tension according to the Test Method 1. Results are in Table 2.

TABLE 2

Surface Tension Measurement

| Concentration, % | Measured Surface Tension, mN/m |
|---|---|
| 0.00000698 | 71.61 |
| 0.0000698 | 71.15 |
| 0.000698 | 65.68 |
| 0.00698 | 70.17 |
| 0.0698 | 62.17 |
| 0.698 | 38.27 |

*Example was added to deionized water by weight based on solids of the additive in DI water; Standard Deviation < 1 dynes/cm; Temperature about 23° C. Normal surface tension of deionized water is 72 dyne/cm.

The data in Table 2 shows that when the above fluoroalkyl ether sulfonate salt surfactant of Example 2 was added at a specified rate, the surface tension of each aqueous solution was reduced.

Comparative Example B

In Comparative Example B, perfluorooctanoic acid was employed having the formula $CF_3CF_2CF_2CF_2CF_2CF_2CF_2COOH$ which was used in the ammonium salt form (ammonium perfluorooctanoate of the formula: $F(CF_2)_7COONH_4$) in the polymerization of copolymers of tetrafluoroethylene (TFE) with perfluoro(alkyl vinyl ether), i.e., perfluoro(propyl vinyl ether) (PPVE). The surfactant solution used was 19% by weight ammonium perfluorooctanoate in deionized water.

The initiator solution used was 1.0 g ammonium persulfate in 1000 g deionized water. Deaerated water was used in the polymerizations. It was prepared by pumping deionized water into a large stainless steel vessel and vigorously bubbling nitrogen gas for approximately 30 minutes through the water to remove all oxygen. The reactor was a 1 Liter vertical autoclave made of Inconel®, equipped with a three-bladed ribbon agitator and a baffle insert. No chain transfer agent was used in this Example. A vacuum of approximately −13 PSIG (11.7 kPa) was applied to the reactor. This was used to draw in a solution of 4.8 g the surfactant solution and 500 mL deaerated water as a precharge. The reactor was then purged three times (agitator=100 RPM) by pressurization with nitrogen gas to 50 PSIG (450 kPa) followed by venting to 1 PSIG (108 kPa) to reduce oxygen content. It was further purged three times (agitator=100 rpm) by pressurization with gaseous tetrafluoroethylene (TFE) to 25 PSIG (274 kPa) followed by venting to 1 PSIG (108 kPa) further insuring that the contents of the autoclave were free of oxygen. The agitator rate was increased to 600 RPM, the reactor was heated to 65° C., and then perfluoro(propyl vinyl ether) (PPVE) (12.8 g) was pumped as a liquid into the reactor. When at temperature, the reactor pressure was raised to a nominal 250 PSIG (1.83 MPa) by adding tetrafluoroethylene (TFE) (~38 g). The initiator solution was fed to the reactor at a rate of 20 mL/min for 1 min. to provide a precharge of 0.02 g ammonium persulfate. It was then pumped at a rate of 0.25 mL/min. until the end of the batch which was defined as the point at which 90 g of TFE has been consumed, measured as mass loss in a TFE weigh tank.

At kickoff (defined as the point at which a 10 PSIG (70 kPa) pressure drop was observed) the polymerization was deemed to have been started, which was also the start point for feeding PPVE at a rate of 0.12 g/min. for the rest of the polymerization. Reactor pressure was kept constant at 250 PSIG (1.83 MPa) by feeding TFE as needed throughout the entire polymerization. After 90 g of TFE had been consumed, the agitator was slowed to 200 RPM, all feeds to the reactor were shut off, and the contents were cooled to 30° C. over the course of 30 minutes. The agitator was then turned down to 100 RPM and the reactor was vented to atmospheric pressure. The fluoropolymer dispersion thus produced had a solids content of around 15-16 wt. %. Polymer was isolated from the dispersion by freezing, thawing and filtration. The polymer was washed with deionized water and filtered several times before being dried overnight in a vacuum oven at 80° C. and a vacuum of 30 mm Hg (4 kPa). The particle size and undispersed coagulum were measured according to Test Methods 3 and 4. Results are reported in Table 5.

Example 3

Following the general procedure of Comparative Example B, the Surfactant Solution used in Example 3 was made from 0.88 g of $C_3F_7OCF_2CF_2CH_2CH_2SO_3Na$ dissolved in 500 mL of deionized water. There was no additional water precharge. Results are reported in Table 5.

Example 4

1 L stainless reactor was charged with distilled water (450 mL), $C_3F_7OCF_2CF_2CH_2CH_2SO_3Na$ (4.0 g), disodium hydrogen phosphate (0.4 g) and ammonium persulfate (0.4 g), followed by introducing tetrafluoroethylene (TFE) (46 g) and perfluoro-(methyl vinyl ether) (PMVE) (39 g). The reactor heated at 70° C. for eight hours under agitation. The polymer emulsion unloaded from the reactor was coagulated with saturated $MgSO_4$ aqueous solution. The polymer precipitate was collected by filtration and washed warm water (70° C.) several times. After drying in vacuum oven (100 mmHg, 13300 Pa) at 100° C. for 24 hours, 54 g of white polymer was obtained. The product was characterized by: Tg: −4° C.; Composition $^{19}F$ NMR (mol %): PMVE/TFE (30.3/69.7).

Example 5

1 L stainless reactor was charged with distilled water (450 mL), $C_3F_7OCF_2CF_2CH_2CH_2SO_3Na$ (3.0 g), disodium hydrogen phosphate (0.4 g) and ammonium persulfate (0.4 g), followed by introducing tetrafluoroethylene (TFE) (40 g) and hexafluoropropylene (HFP) (140 g). The reactor was heated at 70° C. for eight hours under agitation. The polymer emulsion unloaded from the reactor was coagulated with saturated $MgSO_4$ aqueous solution. The polymer precipitate was collected by filtration and washed with warm water (70° C.) several times. After drying in vacuum oven (100 mmHg, 13300 Pa) at 100° C. for 24 hours, 24 g of white polymer was obtained. The product was characterized by: Tm: −260.72° C.; Composition $^{19}F$ NMR (mol %): HFP/TFE (14.4/85.6).

Example 6

A solution of 29.6 g of $C_3F_7OCF_2CF_2CH_2CH_2SO_3Na$, 18.5 g disodium phosphate heptahydrate and 24,900 g of deionized, deoxygenated water was charged to a 40 liter reactor. The solution was heated to 80° C. After removal of trace oxygen, the reactor was pressurized with 2112 grams of a mixture of 3.9 wt % vinylidene fluoride (VF2), 85.7 wt % hexafluoropropene (HFP), and 10.0 wt % tetrafluoroethylene (TFE). At the end of pressurization, the reactor pressure was 2.0 MPa. The reactor was charged with 50.0 ml of an initiator solution of 1% ammonium persulfate and 5% disodium phosphate heptahydrate to start polymerization. As the reactor pressure dropped, a mixture of 35.2 wt % vinylidene fluoride, 36.8 wt % hexafluoropropene, and 28.0 wt % tetrafluoroethylene was fed to the reactor to maintain a 2.0 MPa pressure. After 45 g of this monomer mixture had been fed, 26.0 g of a mixture of 37.29 mol % 1,4-diiodoperfluorobutane, 46.38 mol % 1,6-diiodoperfluorohexane, 11.98 mol % 1,8-diiodoperfluorooctane, and 3.76 mol % 1,10-diiodoperfluorodecane was charged to the reactor. Additional initiator solution was added to maintain polymerization rate. After 3700 g of the monomer mixture had been added, 4-iodo-3,3,4,4-tetrafluorobutene-1 (ITFB) was introduced to the reactor at a feed rate of 5.0 g ITFB per 1000 g monomer. After a total of 8333 g incremental major monomer had been fed, corresponding to a total of 150 ml initiator solution, 20.4 g ITFB and 14.5 hours, monomer and initiator fed was discontinued. The reactor was cooled and the pressure in the reactor reduced to atmospheric. The resulting fluoroelastomer latex had a solids content of 24.5 wt. % solids, a pH of 4.0, and an average particle diameter of 262 nm, measured by BI-9000 Particle Sizing, Brookhaven Instruments Corporation. The latex was coagulated with aluminum sulfate solution, washed with deionized water, and dried. The fluoroelastomer had an inherent viscosity of 0.48 dl/g, a Mooney viscosity, ML (1+10), of 82 and contained 34.6 wt % VF2, 37.3 wt % HFP, 28.0 wt % TFE and 0.22 wt % I.

Example 7

$C_2F_5OCF_2CF_2I$ (116 g, 0.32 mol) and benzoyl peroxide (4 g) were charged under nitrogen. A series of three vacuum/N2 gas sequences were then executed at −50° C., after which ethylene (24 g, 0.86 mol) was introduced. The vessel was heated for 24 hour at 110° C. The autoclave was cooled to 0° C. and opened after degassing. Then the product was collected in a bottle. 6 runs were combined and the product was distilled giving 470 g of $C_2F_5OCF_2CF_2CH_2CH_2I$ in 64% yield. The boiling point of the product was 135~137° C. $C_2F_5OCF_2CF_2CH_2CH_2I$ (195 g, 0.5 mol) was added to the mixture of ethanol (250 mL) and water (250 mL). Sodium sulfite (126 g, 1 mol) was added, followed by 15 g copper. The reaction mixture was stirred vigorously under reflux for a week. 500 mL water was added and filtered at 75° C. The filtrate was cooled and the product $C_2F_5OCF_2CF_2CH_2CH_2SO_3Na$ was collected by filtration as white solid (112 g, 61.2%). The compound was characterized by: $^1H$ NMR (CDCl3, 400 MHz) δ 3.20~3.16 (2H, m), 2.70~2.57 (2H, m); $^{19}F$ NMR (CDCl$_3$, 373 Hz) δ −86.95 (3F, s), −87.97~88.07 (2F, m), −88.71~88.82 (2F, m), −117.72(2F, t, J=18 Hz). The product was added to water and tested for surface tension according to the Test Method 1. Results are in Table 3.

TABLE 3

Surface Tension Measurement

| Concentration, % | Measured Surface Tension, mN/m |
|---|---|
| 1.2156E−06 | 72.54 |
| 0.000012156 | 56.46 |
| 0.00012156 | 69.09 |
| 0.00012156 | 67.98 |
| 0.0012156 | 66.90 |

TABLE 3-continued

Surface Tension Measurement

| Concentration, % | Measured Surface Tension, mN/m |
|---|---|
| 0.0012156 | 67.18 |
| 0.012156 | 65.85 |
| 0.12156 | 56.60 |
| 0.12156 | 56.49 |
| 0.8676 | 48.27 |
| 1.2156 | 39.31 |
| 1.2156 | 38.30 |

*Example was added to deionized water by weight based on solids of the additive in DI water; Standard Deviation < 1 dynes/cm; Temperature about 23° C. Normal surface tension of deionized water is 72 dyne/cm.

The data in Table 3 shows that when the above fluoroalkyl ether sulfonate salt surfactant in Example 7 was added at a specified rate, the surface tension of each aqueous solution was reduced.

Example 8

Following the general procedure of Comparative Example B, the Surfactant Solution used in Example 8 was made from 0.77 g of $C_2F_5OCF_2CF_2CH_2CH_2SO_3Na$ dissolved in 500 mL of deionized water. There was no additional water precharge. Results are reported in Table 5.

Example 9

1 L stainless reactor was charged with distilled water (450 mL), $C_2F_5OCF_2CF_2CH_2CH_2SO_3Na$ (4.0 g), disodium hydrogen phosphate (0.4 g) and ammonium persulfate (0.4 g), followed by introducing tetrafluoroethylene (TFE) (46 g) and perfluoro-(methyl vinyl ether) (PMVE) (39 g). The reactor was heated at 70° C. for eight hours under agitation. The polymer emulsion unloaded from the reactor was coagulated with saturated MgSO$_4$ aqueous solution. The polymer precipitate was collected by filtration and washed warm water (70° C.) several times. After drying in vacuum oven (100 mmHg, 13300 Pa) at 100° C. for 24 hours, 56 g of white polymer was obtained. The product was characterized by: Tg: −7.3° C.; Composition $^{19}F$ NMR (mol %): PMVE/TFE (25.3/74.7)

Example 10

1 L stainless reactor was charged with distilled water (450 mL), $C_2F_5OCF_2CF_2CH_2CH_2SO_3Na$ (3.0 g), disodium hydrogen phosphate (0.4 g) and ammonium persulfate (0.4 g), followed by introducing tetrafluoroethylene (TFE) (40 g) and hexafluoropropylene (HFP) (140 g). The reactor heated at 70° C. for eight hours under agitation. The polymer emulsion unloaded from the reactor was coagulated with saturated MgSO$_4$ aqueous solution. The polymer precipitate was collected by filtration and washed with warm water (70° C.) several times. After drying in vacuum oven (100 mmHg, 13300 Pa) at 100° C. for 24 hours, 36 g of white polymer was obtained. The product was characterized by: Tm: −255.10° C.; Composition $^{19}F$ NMR (mol %): HFP/TFE (11.4/88.6).

Example 11

A solution of 25.6 g of $C_2F_5OCF_2CF_2CH_2CH_2SO_3Na$, 18.5 g disodium phosphate heptahydrate and 24,900 g of deionized, deoxygenated water was charged to a 40 liter reactor. The solution was heated to 80° C. After removal of trace oxygen, the reactor was pressurized with 2092 grams of a mixture of 4.1 wt % vinylidene fluoride (VF2), 85.9 wt % hexafluoropropene (HFP), and 10.0 wt % tetrafluoroethylene (TFE). At the end of pressurization, the reactor pressure was 2.0 MPa. The reactor was charged with 50.0 ml of an initiator solution of 1% ammonium persulfate and 5% disodium phosphate heptahydrate to start polymerization. As the reactor pressure dropped, a mixture of 35.0 wt % vinylidene fluoride, 37.0 wt % hexafluoropropene, and 28.0 wt % tetrafluoroethylene was fed to the reactor to maintain a 2.0 MPa pressure. After 45 g of this monomer mixture has been fed, 26.0 g of a mixture of 37.29 mol % 1,4-diiodoperfluorobutane, 46.38 mol % 1,6-diiodoperfluorohexane, 11.98 mol % 1,8-diiodoperfluorooctane, and 3.76 mol % 1,10-diiodoperfluorodecane was charged to the reactor. Additional initiator solution was added to maintain polymerization rate. After 3700 g of the monomer mixture had been added, 4-iodo-3,3,4,4-tetrafluorobutene-1 (ITFB) was introduced to the reactor at a feed rate of 5.0 g ITFB per 1000 g monomer. After a total of 8333 g incremental major monomer had been fed, corresponding to a total of 115 ml initiator solution, 20.4 g ITFB and 15.4 hours, monomer and initiator fed was discontinued. The reactor was cooled and the pressure in the reactor reduced to atmospheric. The resulting fluoroelastomer latex had a solids content of 24.0 wt. % solids, a pH of 3.9, and an average particle diameter of 383 nm, measured by BI-9000 Particle Sizing, Brookhaven Instruments Corporation. The latex was coagulated with aluminum sulfate solution, washed with deionized water, and dried. The fluoroelastomer had an inherent viscosity of 0.44 dl/g, a Mooney viscosity, ML (1+10), of 67 and contained 35.1 wt % VF2, 36.4 wt % HFP, 28.3 wt % TFE and 0.22 wt % I.

Example 12

A 1-liter Hastelloy C276 reaction vessel was charged with a solution of 22 g potassium sulfite hydrate ($KHSO_3 \cdot xH_2O$, 95%, Aldrich, 0.14 mol), 67.8 g potassium metabisulfite ($K_2S_2O_5$, 99%, Mallinckrodf, 0.31 mol) and 500 mL of deionized water. The vessel was cooled to 7° C., evacuated to −7 PSIG, (48263 Pa), and purged with nitrogen. The evacuate/purge cycle was repeated two more times. To the vessel was then added 150 g perfluoro(propylvinyl ether) (PPVE, 0.57 mol) and it was heated to 125° C. at which time the inside pressure was 125 PSIG. The reaction temperature was maintained at 125° C. for 16 hour, at which point the vessel was cooled to 25° C. and vented. The crude reaction product was a white crystalline precipitate with a colorless aqueous layer (pH=7) above it. $^{19}F$ NMR of the white solid showed pure desired product. The product slurry was cooled to below 5° C. and then suction filtered through a fritted-glass funnel. The wet cake was dried in vacuo (25° C., 100 milliTorr) for 72 h to give the product as a white powder (160 g, 74% yield). Product of the formula $C_3F_7OCHFCF_2SO_3K$ was characterized by: $^{19}F$ NMR ($D_2O$) δ −79.1 (t, $^3J_{FF}$=7 Hz, 3F); −82.8, −84.3 subsplit ABq, $^2J_{FF}$=147 Hz, 2F); −116.8, −118.1 (subsplit ABq, $^2J_{FF}$=258 Hz, 2F); −141.6 (dm, $^2J_{FH}$=53 Hz, 1F).

$^1H$ NMR ($D_2O$) δ 6.7 (dm, $^2J_{FH}$=53 Hz, 1H). Mp (DSC) 235° C. Anal. calc. for $C_5HO_4F_{10}SK$: C, 15.5: H, 0.3: N, 0.0. Found: C, 15.4: H, <0.1: N, 0.35. The product was added to water and tested for surface tension according to the Test Method 1. Results are in Table 4.

TABLE 4

| Surface Tension Measurement | |
|---|---|
| Concentration, % | Measured Surface Tension, mN/m |
| 0.00101 | 72.68 |
| 0.001 | 72.88 |
| 0.0101 | 71.51 |
| 0.01 | 71.74 |
| 0.01 | 71.86 |
| 0.1 | 68.18 |
| 0.1 | 63.98 |
| 0.25256 | 63.42 |
| 1 | 42.36 |
| 2.5 | 31.94 |
| 2.5256 | 35.17 |
| 2.5256 | 34.75 |
| 2.5256 | 34.26 |
| 2.5256 | 33.88 |

*Example was added to deionized water by weight based on solids of the additive in DI water; Standard Deviation < 1 dynes/cm; Temperature about 23° C. Normal surface tension of deionized water is 72 dyne/cm.

The data in Table 4 shows that when the above fluoroalkyl ether sulfonate salt surfactant in Example 12 was added at a specified rate, the surface tension of each aqueous solution was reduced.

Example 13

Following the general procedure of Comparative Example B, the Surfactant Solution used in Example 13 was made from 0.81 g of Potassium-1,1,2-trifluoro-2-(perfluoropropoxy) ethanesulfonate of the formula $C_3F_7OCHFCF_2SO_3K$ dissolved in 500 mL of deionized water. There was no additional water precharge. Results are reported in Table 5.

TABLE 5

| TFE/PPVE Polymerization | | | | | | |
|---|---|---|---|---|---|---|
| Example | Surfactant | Surfactant dry mass (g) | Surfactant mmol | Surfactant ppm | Total Initiator APS (g × $10^{-2}$) | Time to kickoff (min.) | Time to consume 90 g TFE (min.) |
| Comp. B | $F(CF_2)_7COONH_4$ | 0.96 | 2.2 | 1477 | 4.35 | 15 | 79 |
| Comp. B | $F(CF_2)_7COONH_4$ | 0.96 | 2.2 | 1481 | 4.48 | 18 | 81 |
| Comp. B | $F(CF_2)_7COONH_4$ | 0.96 | 2.2 | 1463 | 4.73 | 19 | 90 |
| Comp. B | $F(CF_2)_7COONH_4$ | 0.96 | 2.2 | 1480 | 4.40 | 13 | 83 |
| 3 | $C_3F_7OCF_2CF_2CH_2CH_2SO_3Na$ | 0.88 | 2.1 | 1345 | 4.73 | 12 | 97 |
| 3 | $C_3F_7OCF_2CF_2CH_2CH_2SO_3Na$ | 0.88 | 2.1 | 1356 | 4.80 | 7 | 105 |
| 8 | $C_2F_5OCF_2CF_2CH_2CH_2SO_3Na$ | 0.77 | 2.1 | 1198 | 4.68 | 10 | 97 |
| 8 | $C_2F_5OCF_2CF_2CH_2CH_2SO_3Na$ | 0.77 | 2.1 | 1202 | 4.53 | 9 | 92 |
| 13 | $C_3F_7OCHFCF_2SO_3K$ | 0.81 | 2.2 | 1263 | 4.33 | 10 | 83 |
| 13 | $C_3F_7OCHFCF_2SO_3K$ | 0.81 | 2.2 | 1276 | 4.28 | 15 | 76 |

TABLE 5-continued

TFE/PPVE Polymerization

| Example | % solids | Total batch mass (g) | Total polymer mass (g) | Ave. particle size (nm) | Undispersed polymer (coagulum) g) | Wt. % PPVE |
|---|---|---|---|---|---|---|
| Comp. B | 15.6 | 649.8 | 104.6 | 137 | 3.5 | 4.8 |
| Comp. B | 16.2 | 648.0 | 106.7 | 125 | 1.7 | 5.1 |
| Comp. B | 16.8 | 655.8 | 110.8 | 129 | 1.0 | 5.0 |
| Comp. B | 15.8 | 648.5 | 106.9 | 130 | 4.5 | 4.3 |
| 3 | 16.1 | 645.1 | 103.8 | 138 | 0.7 | 5.0 |
| 3 | 16.1 | 648.9 | 104.5 | 133 | 0.8 | 5.2 |
| 8 | 15.9 | 642.9 | 102.2 | 159 | 3.1 | 4.1 |
| 8 | 16.0 | 640.5 | 102.5 | 160 | 1.6 | 3.9 |
| 13 | 14.9 | 641.4 | 95.6 | 167 | 3.8 | 3.5 |
| 13 | 16.6 | 634.7 | 105.4 | 169 | 2.8 | 3.9 |

The data in Table 5 shows that the Examples of the invention provide comparable performance to Comparative Example B coagulum generated while having less fluorine present.

What is claimed is:

1. A compound of formula (I)

$$R_f-O-(CXX')_m-(CY_2)-SO_3M \quad (1)$$

wherein
  $R_f$ is a $C_1$ to $C_4$ linear or branched perfluoroalkyl group,
  X and X' are each independently H or F, provided that at least one of X or X' is F,
  each Y is independently H,
  m is an integer from 1 to 4,
  n is an integer from 1 to 2, and
  M is H, $NH_4$, Li, Na or K,
provided that when CXX' is CHF or CFH, then n is 2,
said compound having surfactant properties in a liquid.

2. The compound of claim 1 wherein $R_f$ is $C_2F_5$ or $C_3F_7$.

3. The compound of claim 2 wherein m is 2 and n is 2.

4. The compound of claim 3 wherein M is H or Na.

5. The compound of claim 2 wherein X is H and X' is F.

6. A process comprising polymerizing at least one fluorinated olefin monomer in an aqueous medium in the presence of a compound of the formula (1A):

$$R_f-O-(CXX')_m-(CY_2)_n-SO_3M \quad (1A)$$

wherein
  $R_f$ is a $C_1$ to $C_4$ linear or branched perfluoroalkyl group,
  X and X' are each independently H or F, provided that at least one of X or X' is F,
  each Y is independently H or F,
  m is an integer from 1 to 4,
  n is an integer from 1 to 2, and
  M is H, $NH_4$, Li, Na or K,
to form an aqueous dispersion of fluoropolymer.

7. The process of claim 6 wherein said compound of formula (1A) is present in said aqueous medium in an amount of from about 0.01% to about 10% based on the weight of water in said aqueous medium.

8. The process of claim 6 wherein said aqueous dispersion of fluoropolymer formed has a fluoropolymer solids content of at least about 10% by weight.

9. The process of claim 6 wherein said aqueous medium is substantially free of perfluoropolyether oil.

10. The process of claim 6 wherein said polymerization medium is substantially free of fluoropolymer seed at polymerization kick-off.

11. The process of claim 6 wherein said polymerizing produces less than about 10% by weight undispersed fluoropolymer based on the total weight of fluoropolymer produced.

12. The process of claim 6 wherein the fluoropolymer has chemical stability in an acidic, oxidizing or reducing medium.

13. The process of claim 6 wherein the fluoropolymer is an elastomer.

14. A method of altering the surface behavior of a liquid comprising adding to the liquid the composition of a compound of formula (1A):

$$R_f-O-(CXX')_m-(CY_2)_n-SO_3M \quad (1A)$$

wherein
  $R_f$ is a $C_1$ to $C_4$ linear or branched perfluoroalkyl group,
  X and X' are each independently H or F, provided that at least one of X or X' is F,
  each Y is independently H or F,
  m is an integer from 1 to 4,
  n is an integer from 1 to 2, and
  M is H, $NH_4$, Li, Na or K.

15. The method of claim 14 wherein the surface behavior is selected from the group consisting of wetting, antistatic, antifoaming, penetration, spreading, leveling, flowing, emulsifying, dispersing, repelling, releasing, lubricating, etching, bonding, and stabilizing.

16. The method of claim 14 wherein the liquid is a coating composition, battery composition, fire-fighting agent, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor finish, or bonding agent.

17. The method of claim 14 wherein the liquid is an acidic, oxidizing or reducing media.

* * * * *